United States Patent [19]

Rodder

[11] 4,262,689
[45] Apr. 21, 1981

[54] RESPIRATOR VALVE

[76] Inventor: Jerome A. Rodder, 775 Sunshine Dr., Los Altos, Calif. 94022

[21] Appl. No.: 951,167

[22] Filed: Oct. 13, 1978

[51] Int. Cl.$^3$ .......................... F16K 5/10; F16K 5/22
[52] U.S. Cl. .............................. 137/246.12; 137/312; 137/887; 251/209
[58] Field of Search ................... 137/312, 246.12, 887; 251/309, 314, 209

[56] References Cited

U.S. PATENT DOCUMENTS

| | | | |
|---|---|---|---|
| 978,706 | 12/1910 | Davidson | 251/138 |
| 2,067,346 | 1/1937 | Rovinsky | 251/209 X |
| 3,092,146 | 6/1963 | Plass | 251/209 X |
| 3,126,916 | 3/1964 | Ducey | 137/246.12 X |
| 3,233,865 | 2/1966 | Panzica et al. | 251/309 |

*Primary Examiner*—Arnold Rosenthal
*Attorney, Agent, or Firm*—Christie, Parker & Hale

[57] ABSTRACT

A stator has a cylindrical bore. A cylindrical rotor fits in the bore with a clearance. A circumferential groove varying in depth is formed around the circumference of the rotor. Ball bearings support the rotor for rotation in spaced relationship from the bore without a seal. Axially elongated inlet and outlet slots are formed in the stator so as to communicate with the groove at circumferentially spaced points. Vent holes lead from the bore to the exterior of the stator between the inlet and outlet and the ball bearings. The valve is coupled by first and second legs of a tee connection to a patient. A third leg of the tee connection is connected by a needle valve to a vacuum source.

17 Claims, 4 Drawing Figures

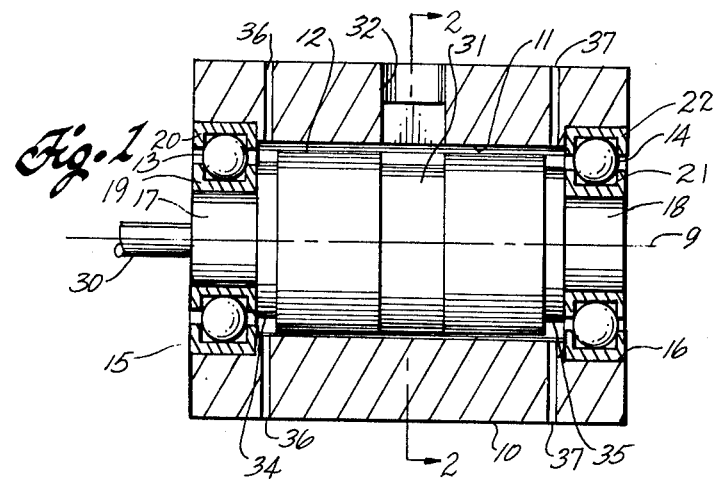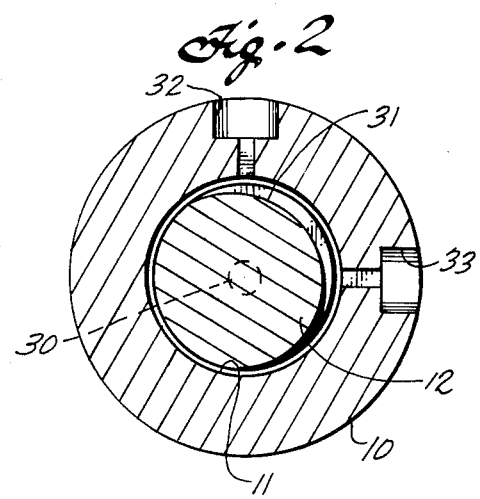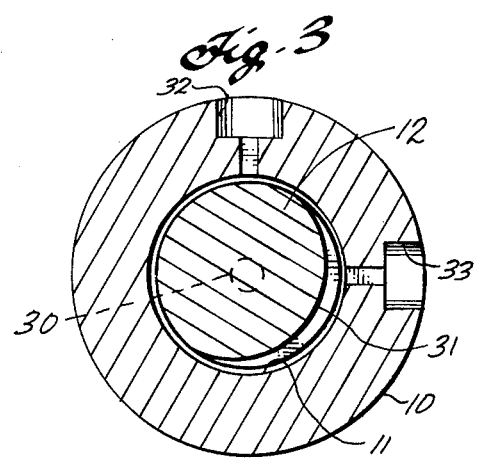

RESPIRATOR VALVE

BACKGROUND OF THE INVENTION

This invention relates to medical equipment and, more particularly, to a valve that controls a respirator.

My copending application Ser. No. 936,380, filed Aug. 24, 1978, discloses a sensitive bipolar flowmeter for measuring the gas flow rate between a respirator and a patient. One type of respirator comprises a bellows that is expanded and contracted to control gas flow to the patient. The volume change of the bellows and the volume of gas received by the patient are not accurately related. Control valves are not commonly used in a regulator because the seals and rubbing parts of such valves are subject to wear and thus require frequent maintenance. The inertia of moving parts also increases the response time when functioning in an automatic control system. In addition, contamination of the gas supplied to the patient by the lubricant for the rubbing parts of the valve is a danger.

SUMMARY OF THE INVENTION

According to the invention, a respirator valve has a valve body member with a cylindrical bore, a cylindrical control member fitting in the bore with a clearance, and a pair of spaced apart lubricated bearings for supporting the control member in spaced relationship from the bore for relative rotation between the members without a seal therebetween. An inlet and an outlet are formed in one member between the pair of bearings to open into the space between the control member and the bore at circumferentially spaced apart points. Passages lead from the bore to the exterior of the body member between the inlet and the outlet and the bearings. As a result, the valve is vented in a manner that inhibits removal of the bearing lubricant by leakage gas. A circumferential groove is formed around the surface of the other member to to communicate with the inlet and outlet. The flow resistance presented by the groove between the inlet and outlet changes as a function of the angular displacement between the members. Continual leakage takes place through the space between the control member and bore to the outlet and the atmosphere. The result is a sealless, low inertia, almost frictionless respirator valve having only one moving part, e.g., the rotatable member.

Preferably, the described regulator valve is coupled to the patient by a tee connection having one leg coupled by a needle valve to a vacuum pump. The vacuum pump continually draws gas from the tee connection to compensate for the leakage flow through the valve.

A feature of the invention is the provision of an inlet and an outlet in the form of axially extending slots, which permits a wide range of flow control without unduly restricting the maximum flow rate.

BRIEF DESCRIPTION OF THE DRAWINGS

The features of a specific embodiment of the best mode contemplated of carrying out the invention are illustrated in the drawings, in which:

FIG. 1 is a side, partially sectional view of a regulator valve incorporating the principles of the invention;

FIG. 2 is an end sectional view of the valve of FIG. 1 through a plane 2—2 in one angular position of the control member;

FIG. 3 is an end sectional view of the valve of FIG. 1 through plane 2—2 in another angular position of the control member.

DETAILED DESCRIPTION OF THE SPECIFIC EMBODIMENT

Figure 4:
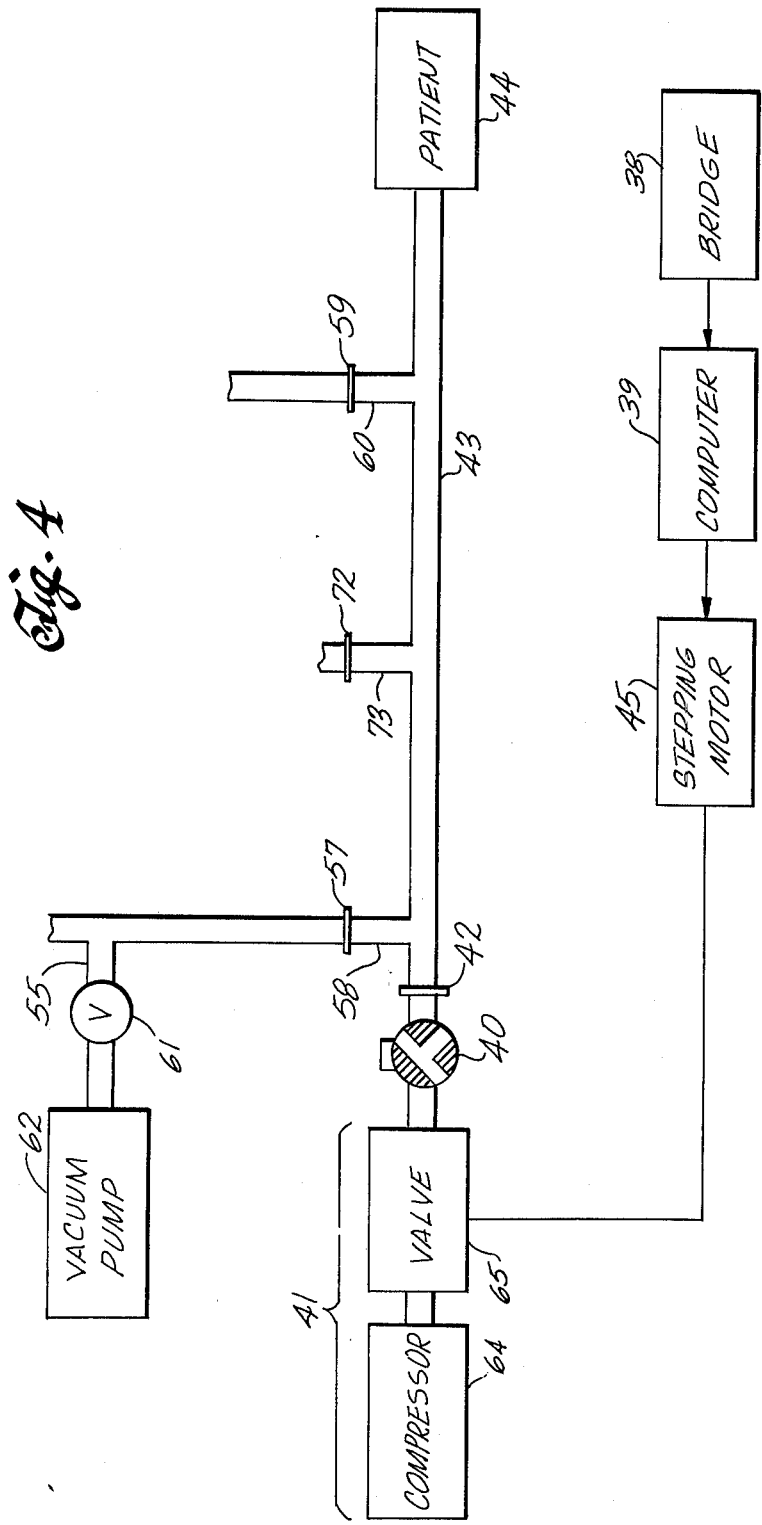
FIG. 4 is a schematic block diagram of a portion of a regulator system incorporating the valve of FIG. 1.

In FIGS. 1, 2, and 3, a regulator valve comprises a stationary valve body member 10 that has a cylindrical bore 11, and a cylindrical control member 12 that fits in bore 11 with a clearance. Lubricated ball bearings 13 and 14 at either end of control member 12, support control member 12 for rotation about an axis 9 relative to body member 10 in spaced relationship from bore 11. Ball bearings 13 and 14 lie, between inner races 19 and 21, respectively, and outer races 20 and 22, respectively. Outer races 20 and 22 are secured in counterbores 15 and 16, respectively, in the ends of bore 11. Inner races 19 and 21 are secured in cylindrical bearing mounts 17 and 18, respectively, of control member 12, which are of reduced diameter. The only contact between moving parts is that between the bearings and their races; there is no seal between body member 10 and control member 12. A shaft 30 is attached to one end of control member 12 to adjust the angular position of control member 12 relative to body member 10. The cylindrical surface of bore 11 and the cylindrical surface of control member 12 define a small annular space between body member 10 and control member 12 all the way around their adjacent cylindrical surfaces. In a typical embodiment, bore 11 would have an inch and one half diameter and control member 12 would have a diameter that is 0.002 of an inch smaller than bore 11; thus, the clearance or annular space therebetween would be 0.001 of an inch.

A circumferential groove 31 of varying depth is formed on the cylindrical surface of control member 12, generally in a plane perpendicular to axis 9. Thus, groove 31 forms an eccentric surface around part of the periphery of control member 12. Preferably, the depth of groove 31 increases gradually, i.e., is tapered, from both ends to the middle. The depth of groove 31 is greatly exaggerated in the drawings for the purpose of illustration. Typically, groove 31 would vary in depth between 0.005 of an inch and 0.001 of an inch.

An inlet 32 and an outlet 33 are formed in body member 10, generally in the plane of groove 31. Inlet 32 and outlet 33 extend radially from the exterior of body member 10 to bore 11 and are positioned axially in alignment with groove 31 to permit communication therewith. Generally, the angle between inlet 32 and outlet 33 would be between 90° and 120°, and groove 31 would extend around approximately 180° of the periphery of control member 12. Inlet 32 and outlet 33 each have a cylindrical bore portion opening to the exterior of body member 10 and an axially elongated slot portion opening to bore 11. The bore portions of inlet 32 and outlet 33 are adapted to receive tubing, thereby providing a means of connection to the valve. The slot portions of inlet 32 and outlet 33, which are equal in length to the width of groove 31, provide relatively unrestricted access to and from groove 31 without reducing the range of flow control. For example, if the entire length of inlet 32 and outlet 33 were cylindrical and were equal in diameter to the width of groove 31, the usable angle between inlet 32 and outlet 33 would be less than that shown in FIGS. 2 and 3 and the range of flow control would be correspondingly reduced. If, on the other hand, the entire length of inlet 32 and outlet 33 were cylindrical and equal in diameter to the width of the slot portions, the inlet and outlet would form an inefficient restriction.

Portions 34 and 35 of intermediate diameter are formed near the ends of control member 12. A plurality of radial venting holes 36 and 37 are formed in body member 10 adjacent to portions 34 and 35, respectively. Holes 36 and 37 vent gas from the annular space between portions 34 and 35 and bore 11 to the atmosphere exterior to the valve, thereby preventing gas from passing over bearings 13 and 14.

In operation, gas under pressure supplied to inlet 32 leaks continually to outlet 33 and to the atmosphere through venting holes 36 and 37 by virtue of the clearance between bore 11 and control member 12 and the absence of a seal. Little gas leaks past ball bearings 13 and 14, however. As a result, the lubricant for ball bearings 13 and 14 is not readily removed by the leaking gas. An actuator is connected to shaft 30 to angularly adjust control member 12. The flow rate from inlet 32 to outlet 33 depends upon the angular position of control member 12 because, as depicted by FIGS. 2 and 3, the flow resistance presented by groove 31 is a function of the angular displacement between control member 12 and body member 10.

FIG. 4 represents a portion of the spirometer disclosed in my above referenced copending application. The disclosure of this copending application is incorporated fully herein by reference. The same reference numerals are used to identify the same elements. Respirator 41 comprises a compressor 64 and the valve shown in FIG. 1 herein, represented by a block 65. Valve 65 is coupled by tee connection 58 to a patient represented by block 44. With valve 65 in its minimum flow position, needle valve 61 is adjusted to establish the desired flow rate to or from the patient. Usually, needle valve 61 would be adjusted for a zero flow rate to the patient when valve 65 is in its minimum flow position. The leakage flow is in effect compensated for by vacuum pump 62, which withdraws it from tee connection 58. Thus, even though there is leakage flow through valve 65 at all times, this does not affect the gas flow rate to and from the patient. Alternatively, needle valve 61 could be adjusted to provide gas flow to or from the patient in the minimum flow position of valve 65.

After needle valve 61 is adjusted as described above to cancel the leakage flow from the gas supplied to the patient, the output of the electrical bridge including hot wires $R_1$ through $R_4$, which is represented by a block 38, is connected to the input of a computer 39. Computer 39 controls a stepping motor 45, which drives the control member of valve 65. The output of electrical bridge 38 represents the actual flow rate to the patient. Computer 39 compares the actual flow rate with a desired value and generates an error signal that actuates stepping motor 45, thereby changing the angular position of the control member of valve 37 and the actual value of the flow rate to the patient to bring the actual value into line with the desired value. Thus, valve 65 is functioning in an automatic control system, where its small inertia permits fast response to changing conditions.

In summary, a regulator valve is designed to continually leak for the sake of seal elimination and friction and inertia reduction. The leaking gas bypasses the bearings and, therefore, does not tend to remove their lubrication and further ensures that no lubrication contaminates the patient. The valve is coupled to the patient by a tee connection, one leg of which is connected to a vacuum pump. By adjusting the flow rate of the gas withdrawn by the vacuum pump, leakage gas can be kept from the patient.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention. For example, body member 11 could serve as the rotor instead of control member 12, and control member 12 could serve as the stator instead of body member 10. Further, groove 31 could be formed on body member 10 or inlet 32, and outlet 33 could be formed in control member 12. A tee connection having one leg connected by a needle valve to a vacuum pump could be used to couple leaky respirator valves constructed differently from that disclosed to a patient.

What is claimed is:

1. A respirator valve comprising:
   a first member having a cylindrical bore with a first cylindrical surface;
   a second cylindrical member with a second cylindrical surface, the second member fitting inside the bore of the first member with a small clearance such that the first and second cylindrical surfaces lie adjacent to each other;
   lubricated bearings on either side of the inlet and outlet openings for rotatably supporting the first and second members with respect to each other in axial alignment about an axis of rotation to form a small unsealed annular space between the first and second cylindrical surfaces;
   passage means leading from the annular space to the exterior of the first member between the inlet and the outlet and the bearings;
   an inlet opening into the annular space through one of the cylindrical surfaces;
   an outlet opening into the annular space through the one cylindrical surface; and
   a groove formed in the other cylindrical surface between the inlet and the outlet to vary the flow resistance between the inlet and the outlet as a function of the angular displacement between the first and second members.

2. The valve of claim 1, in which the outlet opens into the annular space at a point circumferentially displaced from the point where the inlet opens into the space.

3. The valve of claim 2, in which the inlet and outlet open into the space at points lying in a plane perpendicular to the axis of rotation.

4. The valve of claim 3, in which the groove has a variable depth.

5. The valve of claim 4, in which the depth of the groove is tapered.

6. The valve of claim 5, in which the groove is longer than the distance through the annular space between the inlet and the outlet.

7. The valve of claim 6, in which the first member is stationary, the second member is rotatable, the inlet and outlet are formed in the stationary member and open into the space through the first cylindrical surface, and the groove is formed in the second cylindrical surface.

8. The valve of claim 7, additionally comprising a stepping motor and a shaft coupling the stepping motor to the second member.

9. The valve of claim 1, additionally comprising a stepping motor and a shaft coupling the stepping motor to one of the members.

10. The valve of claim 1, in which the inlet comprises an axially elongated slot approximately equal in length to the width of the groove.

11. The valve of claim 10, in which the outlet comprises an axially elongated slot approximately equal in length to the width of the groove.

12. The valve of claim 1, additionally comprising a vacuum source, a needle valve, and a tee connection, the tee connection having a first leg connected to the outlet, and a second leg connected by the needle valve to the vacuum source.

13. A respirator valve comprising:
a stator having a cylindrical bore;
a cylindrical rotor fitting in the bore with a clearance;
a circumferential groove constant in width and varying in depth around the circumference of the rotor;
bearing means for supporting the rotor for rotation in spaced relationship from the bore without any seal;
an inlet port formed in the stator so as to communicate with the groove; and
an outlet port formed in the stator so as to communicate with the groove at a point spaced circumferentially from the inlet, one of the ports comprising an axially elongated slot approximately equal in length to the width of the groove.

14. The valve of claim 13, in which the other port also comprises an axially elongated slot approximately equal in length to the width of the groove.

15. The valve of claim 13, in which the bearing means comprise lubricated bearings on either side of the inlet and outlet ports, and passage means leading from the clearance to the exterior of the stator between the inlet and outlet ports and the bearings.

16. The valve of claim 1, in which the second member has a region of reduced diameter adjacent to the passage means to provide a path having small flow resistance to the passage means.

17. The valve of claim 15, in which the rotor has regions of reduced diameter adjacent to the passage means to form an annular space providing low flow resistance to the passage means.

* * * * *